United States Patent [19]

Kobori et al.

[11] Patent Number: 4,656,307
[45] Date of Patent: Apr. 7, 1987

[54] DERIVATIVE OF BRENDANE AND PROCESS FOR PREPARING THE SAME

[75] Inventors: Yoshihiro Kobori, Fujisawa; Tetsuya Takezono, Yokohama, both of Japan

[73] Assignee: Nippon Oil Co., Ltd., Tokyo, Japan

[21] Appl. No.: 755,241

[22] Filed: Jul. 15, 1985

[30] Foreign Application Priority Data

Aug. 3, 1984 [JP] Japan ................... 59-162861

[51] Int. Cl.⁴ ............... C07C 69/757; C07C 61/12
[52] U.S. Cl. ............................... 560/117; 560/114; 562/497; 562/499
[58] Field of Search ............. 560/117, 114; 562/499, 562/497

[56] References Cited

PUBLICATIONS

Hirao et al., Tetrahedron Letters, 1976, pp. 3895-3898.
Hirao et al., Heterocycles, vol. 7, No. 2, 1977, pp. 857-862.

Primary Examiner—Natalie Trousof
Assistant Examiner—Patricia M. Scott
Attorney, Agent, or Firm—Jordan and Hamburg

[57] ABSTRACT

According to the invention a derivative of brendane is provided. The derivative of brendane is represented by the general formula of:

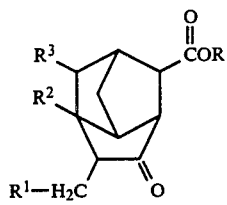

wherein R is a hydrogen atom or a hydrocarbon group having 1 to 6 carbon atoms, and $R^1$ to $R^3$ each represent a hydrogen atom or a methyl group. The brendane derivative is prepared by reacting an alkenylnorbornene of the general formula of:

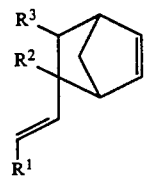

wherein $R^1$ to $R^3$ each represent a hydrogen atom or a methyl group, with carbon monoxide and an alcohol or water in the presence of a catalyst of Group VIII metal compound of the periodic table.

1 Claim, 3 Drawing Figures

DERIVATIVE OF BRENDANE AND PROCESS FOR PREPARING THE SAME

BACKGROUND OF THE INVENTION

1. Field of the Invention;

The present invention relates to derivatives of brendane and a process for preparing the same. More particularly, the present invention is directed to novel derivatives of brendane represented by the following general formula [I] and having utilities as medicines, perfumes and starting materials therefor.

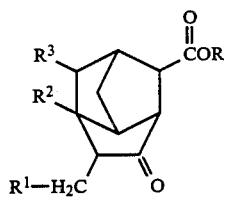

wherein R is a hydrogen atom or a hydrocarbon group having 1 to 6 carbon atoms, and $R^1$ to $R^3$ each represent a hydrogen atom or a methyl group.

2. Prior Art;

Derivatives of tricyclic hydrocarbons are important as medicines, perfumes and starting materials therefor. However, they are prepared generally through extremely complicated processes from very expensive starting materials, and hence have almost no industrial values. Complicated production processes and high costs for these materials pose obstacles for development and production of novel medicines and perfumes. Under these circumstances, there is a demand for a novel derivative of tricyclic hydrocarbon which is inexpensive and can be prepared by a simple process.

OBJECTS AND SUMMARY OF THE INVENTION

A primary object of this invention is to provide a novel derivative of brendane which is important as medicines, perfumes and starting materials therefor, and to provide a process for preparing the same.

Another object of this invention is to provide a derivative of brendane which can be prepared from inexpensive starting materials through a simplified one-step reaction, and to provide a process for the preparation thereof.

A further object of this invention is to provide a novel derivative of brendane and a process for the preparation thereof, the derivative of brendane provided by the invention having intramolecular functional groups so that it may be used as a starting material for synthesizing a variety of other tricyclic hydrocarbon derivatives.

A still further object of this invention is to provide a derivative of brendane which can be subjected to skeletal isomerization reaction, and to provide a process for the preparation thereof.

The above and other objects of this invention will become apparent from the following detailed description.

According to the present invention there is provided a novel derivative of brendane represented by the following general formula [I] of:

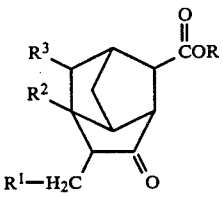

wherein R is a hydrogen atom or a hydrocarbon group having 1 to 6 carbon atoms, and $R^1$ to $R^3$ each represent a hydrogen atom or a methyl group.

Also provided in accordance with the present invention is a process for preparing a derivative of brendane represented by the following general formula [I] of:

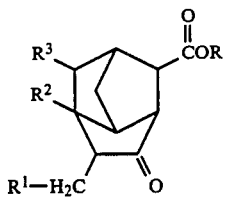

wherein R is a hydrogen atom or a hydrocarbon group having 1 to 6 carbon atoms, and $R^1$ and $R^3$ each represent a hydrogen atom or a methyl group; comprising the step of reacting an alkenylnorbornene represented by the following general formula [II] of:

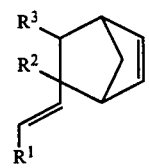

wherein $R^1$ to $R^3$ each represent a hydrogen atom or a methyl group; with carbon monoxide and the one selected from the group consisting of alcohols and water in the presence of a catalyst which is a compound of a metal of Group VIII of the periodic table.

DESCRIPTION OF THE INVENTION

Figure 1:
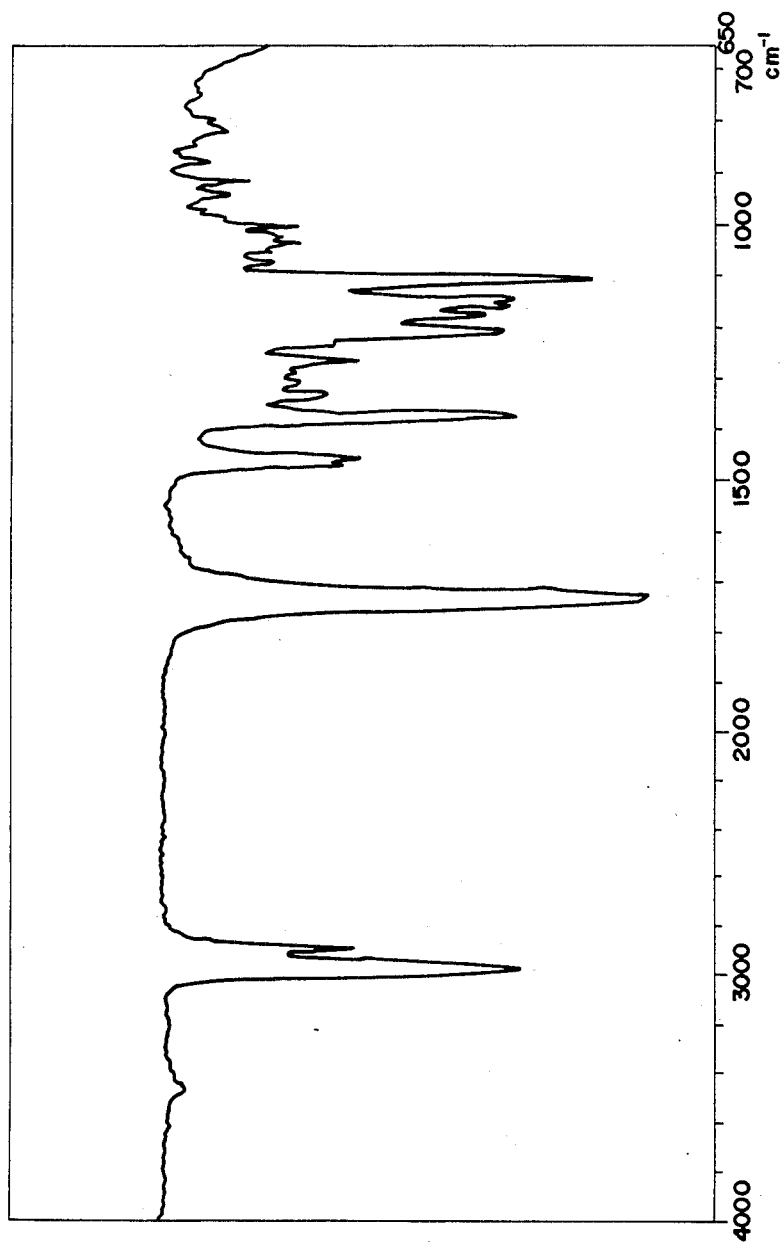
FIG. 1 is an infrared absorption spectrum chart of isopropyl 5-methylbrendane-4-one-2-carboxylate prepared by Example 1 of the invention.

The invention will be described in detail hereinafter.

After eager pursuits for the provision of a novel tricyclic hydrocarbon derivative which can be prepared from inexpensive starting materials through a simple process, we have found that novel derivatives of brendane represented by the following general formula [I] can be prepared from alkenylnorbornenes produced by the Diels-Alder reaction between cyclopentadiene and conjugated diene compounds by reacting the alkenylnorbornenes with carbon monoxide and water or an alcohol in the presence of a catalyst made of a compound of a metal of Group VIII of the periodic table.

The present invention has been accomplished on the basis of this finding.

The derivatives of brendane, provided by the present invention, are represented by the general formula [I] of:

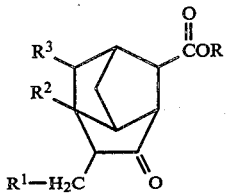

[I]

wherein R is a hydrogen atom or a hydrocarbon group having 1 to 6 carbon atoms, and $R^1$ to $R^3$ each represent a hydrogen atom or a methyl group.

R in the general formula [I] representing the compounds provided by the present invention is a hydrogen atom or a hydrocarbon group having 1 to 6 carbon atoms, the specific examples of the hydrocarbon group being methyl, ethyl, n-propyl, isopropyl, sec-butyl, n-pentyl, n-hexyl and cyclohexyl groups.

The compounds of the invention are novel derivatives of brendane each having a tricyclic hydrocarbon skeleton. Tricyclic hydrocarbon derivatives, such as patchouli alcohol and adamantane derivatives, are generally used as medicines, perfumes and starting materials therefor in a wide application range. However, in general, such tricyclic hydrocarbon derivatives are necessarily prepared from expensive starting materials through extremely complicated procedures to devaluate the industrial merits thereof. On the contrary, the compounds of the invention may be prepared from vinylnorbornenes produced by the Diels-Alder reaction between cyclopentadiene and conjugated diene compounds by reacting the vinylnorbornenes with carbon monoxide and a hydroxyl group-containing compound selected from the group consisting of water and alcohols in the presence of a catalyst made of a compound of a metal of Group VIII of the periodic table. Accordingly, the compounds of the invention can be prepared from inexpensive materials through a far simpler process. This is one of the important features of this present invention. Moreover, each molecule of the compounds of this invention has two functional groups, i.e. a ketone site and a carboxylic acid residue site. A great diversity of different tricyclic hydrocarbon derivatives may be easily synthesized from the compounds of this invention, accordingly. This is a further important merit of the present invention. Furthermore, the compounds of this invention may be subjected to skeletal isomerization reaction to prepare other tricyclic hydrocarbons having different skeletal structures. As should be appreciated from the foregoing, the compounds of this invention can be utilized as extremely valuable starting materials for a variety of novel medicines and perfumes.

The process for preparing the compounds of this invention will now be described.

The compound of this invention represented by the general formula [I] may be prepared by reacting an alkenylnorbornene represented by the following general formula [II] of:

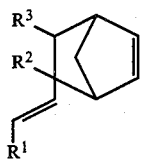

[II]

wherein $R^1$ to $R^3$ each represent a hydrogen atom or a methyl group; with carbon monoxide and water or an alcohol in the presence of a catalyst made of a compound of a metal of Group VIII of the periodic table.

The alcohols used in the process for the preparation of the compounds of this invention are alcohols having 1 to 6 carbon atoms, such as methanol, ethanol, n-propanol, isopropanol, sec-butanol, n-pentanol, n-hexanol and cyclohexanol.

The catalysts used in the synthesis of the compounds of this invention are compounds of metals of Group VIII of the periodic table, and include compounds of cobalt and palladium.

Examples of usable cobalt compounds are cobalt carbonyl complexes, and cobalt compounds which form cobalt carbonyl complexes during the reaction or by proper treatment can be used as effective catalysts. The reaction may be carried out at a carbon monoxide pressure of from 1 kg/cm$^2$ to 500 kg/cm$^2$, preferably from 50 kg/cm$^2$ to 300 kg/cm$^2$, and at a temperature from 30° to 300° C., preferably from 100° to 200° C., while using an aromatic tertiary amine, such as pyridine or isoquinoline, as a promotor catalyst. The aromatic tertiary amine may be used in an amount of 1 to 1000 times, preferably 3 to 100 times, as much as the atom equivalent of cobalt contained in the used catalyst.

An example of a palladium compound catalyst is a palladium complex stabilized with an organic tertiary phosphine. The reaction may be carried out at a carbon monoxide pressure of from 1 kg/cm$^2$ to 500 kg/cm$^2$, preferably from 5 kg/cm$^2$ to 300 kg/cm$^2$, and at a temperature of from 30° to 300° C., preferably from 50° to 150° C. The organic tertiary phosphines which may be used in the process of this invention include organic tertiary phosphines providing catalysts having desirous activities under the reaction condition, the examples being triphenylphosphine (represented by PPh$_3$, wherein Ph is phenyl), tributylphosphine [P(C$_4$H$_3$)$_3$] and methyldiphenylphosphine [represented by CH$_3$P(Ph)$_2$]. It is desious that 1 to 100 times, preferably 2 to 20 times, as much as the quantity of the existing palladium, in molar base, of a phosphine is used. It is estimated that palladium is in the zero equivalency state during the reaction and forms a complex represented by PdL$_x$(CO)$_{4-x}$ (wherein L is generally an organic tertiary phosphine ligand, and x is zero or an integer of 1 to 4). However, palladium may be introduced in an initial catalyst form of other than the zero equivalency state, and it may be introduced, for example, in the forms of Pd(acetate)$_2$, Pd(acetylacetate)$_2$, PdCl$_2$, PdCl$_2$(triphenylphosphine)$_2$ and Pd(triphenylphosphine)$_4$.

An alcohol or water may be present in an amount of not less than equimolecular to the alkenylnorbornene, and a large excessive amount of an alcohol or water may be used without any problem. The reaction may proceed either in a batch process or continuous process depending on the circumstances.

By the reaction described above, one molecule of an alkenylnorbornene is reacted with two molecules of carbon monoxide and one molecule of an alcohol or water to produce a compound of this invention.

The reaction is a single step reaction perfectly, and the compounds of this invention can be prepared extremely easily through the reaction.

EXAMPLES

The present invention will be described more specifically by referring to some Examples thereof.

EXAMPLE 1

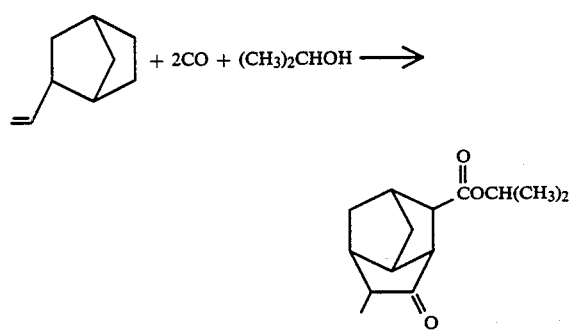

Into a 500 ml stainless steel autoclave charged were 72 g (0.6 mol) of 5-vinyl-2-norbornene, 4.15 g (12 millimols) of $Co_2(CO)_8$, 18 g (0.22 mol) of pyridine and 240 ml of isopropanol. 160 kg/cm$^2$ of carbon monoxide was introduced in the autoclave at the room temperature, and the temperature of the content in the autoclave was raised to 150° C. The reaction was continued at that temperature for 5 hours, and the content was allowed to stand for cooling and then discharged from the autoclave. The reaction product discharged from the autoclave was subjected to rectification to obtain 6.6 g of a fraction of 119°–120° C. (1 mmHg). The chemical structure of that fraction was analyzed by the ultimate analysis, infrared spectrophotometry and NMR spectrophotometry, to confirm that the fraction was isopropyl 5-methylbrendane-4-one-2-carboxylate.

Figure 2:
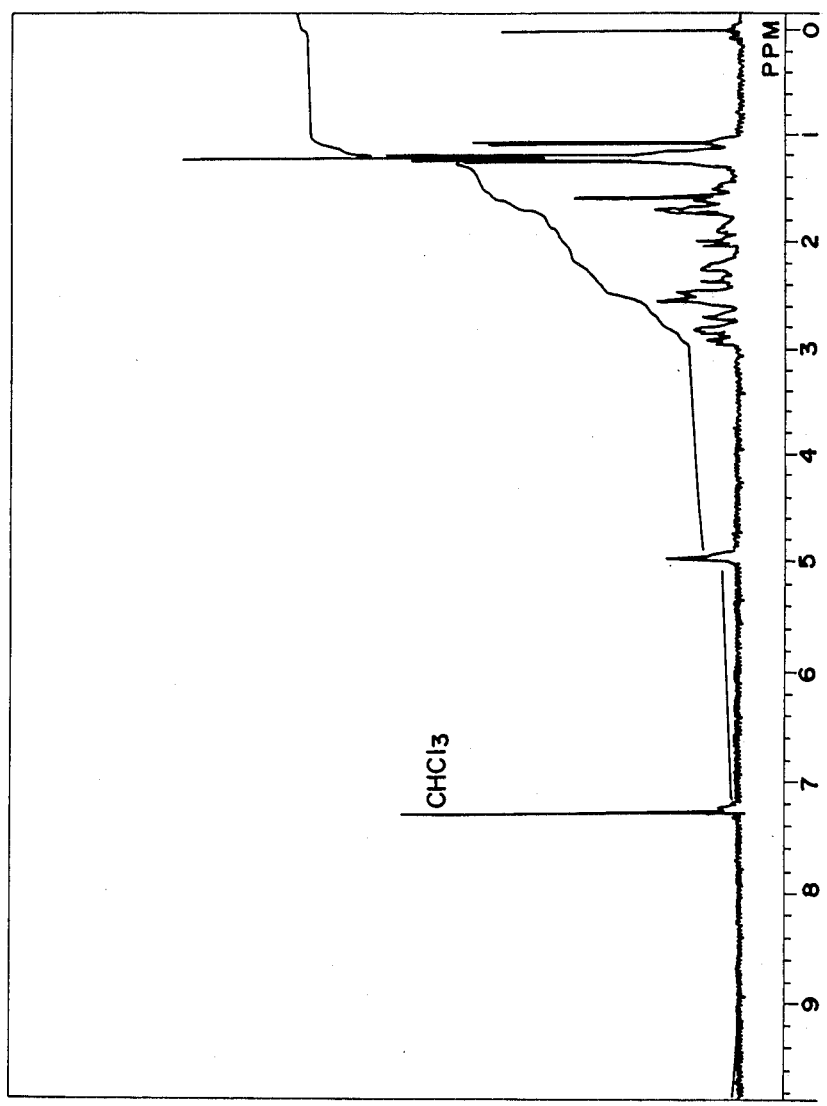
FIG. 2 is an H-NMR chart of the same compound.
Figure 3:
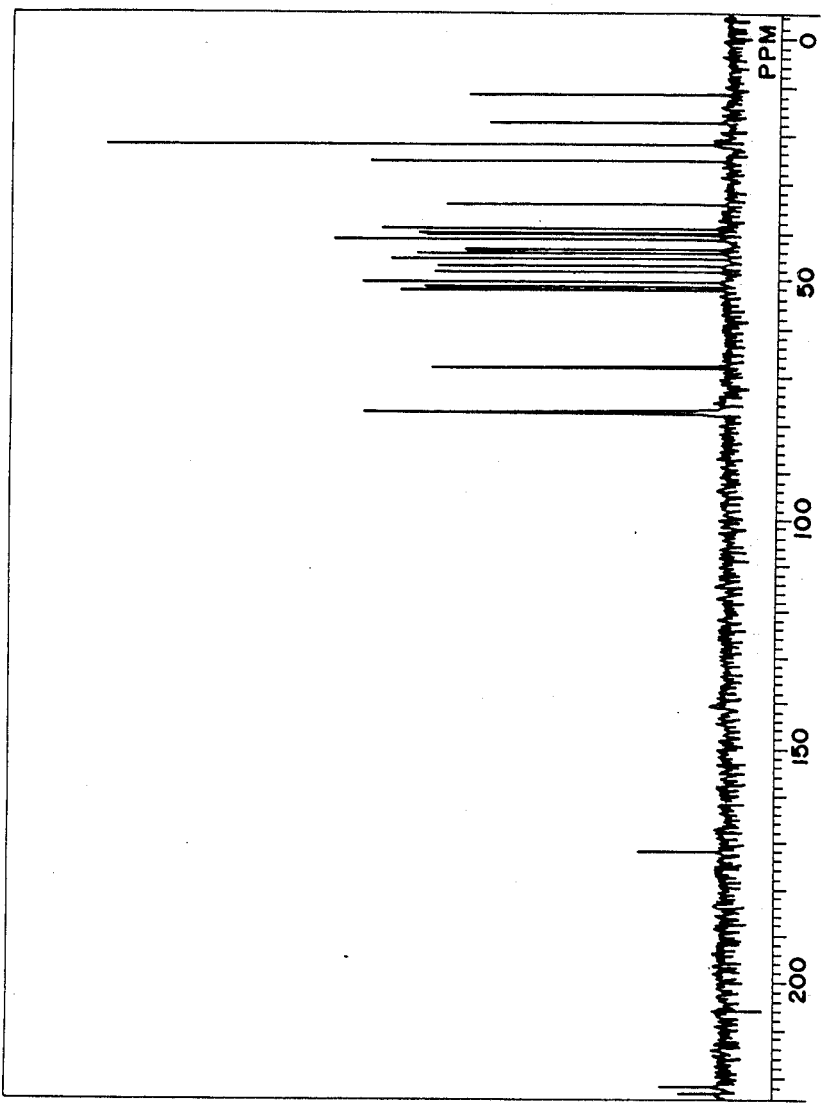
FIG. 3 is a $^{13}$C-NMR chart of the same compound.

FIG. 1 is an infrared spectrum chart (the abscissa in the Figure is calibrated in cm$^{-1}$) of the thus produced isopropyl 5-methylbrendane-4-one-2-carboxylate. FIG. 2 is an H-NMR chart of the same compound (the abscissa in the Figure indicates the δ values in TMS standard), and FIG. 3 is a $^{13}$C-NMR chart (the abscissa in the Figure indicates the δ values in TMS standard) of the same compound. Mass Spectrum m/e (hereinafter referred to simply as MSm/e): 236

Ultimate Analysis ($C_{14}H_{20}O_3$): Cald. (%): C; 71.2, H; 8.5, O; 20.3. Found (%): C; 71.0, H; 8.6, O; 20.4.

Infrared Spectrum Absorption Positions (Liquid Film Method, cm$^{-1}$, hereinafter referred to simply as IR): 2960, 2875, 1730, 1720, 1460, 1450, 1370, 1200, 1100.

H-NMR (400 MHz, CDCl$_3$), δ value (ppm) 1.05–1.25 (CH$_3$, 9H), 1.4–3.0 (CH, CH$_2$, 10H), 4.95 (CH, 1H).

$^{13}$C-NMR (100 MHz, CDCl$_3$), δ value (ppm) 222.8, 221.5 (carbonyl, ketone), 171.63, 171.56 (carbonyl, ester), 68.02 (3), 67.80 (3), 52.00 (3), 51.87 (3), 51.32 (3), 50.42 (3), 48.20 (3), 46.89 (3), 45.23 (3), 44.23 (3), 43.35 (3), 41.11 (3), 41.05 (3), 40.31 (3), 39.95 (2), 39.09 (2), 33.98 (2), 25.20 (2), 21.76 (1), 21.71 (1), 17.19 (1), 11.46 (1).

The numerals in the parentheses indicate, respectively, primary, secondary and tertiary carbon. The result of the $^{13}$C-NMR analysis shows that the product of the invention is a mixture of two isomers. The compound was analysed in detail by the H-NMR to reveal that the product was a miture of isopropyl endo-5-methylbrendane-4-one-2-carboxylate and isopropyl exo-5-methylbrendane-4-one-2-carboxylate mixed in a ratio of approximately 1:1.

EXAMPLE 2

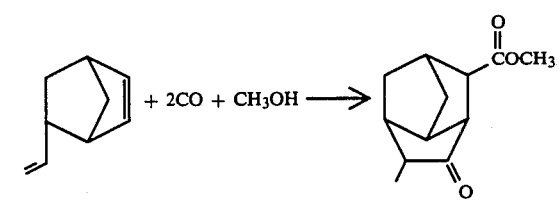

A similar reaction was carried out as in Example 1, except that 240 ml of methanol was used in place of isopropanol, and then the reaction product was subjected to distillation to obtain 0.2 g of a fraction of 104°–105° C. (1 mmHg). The fraction was added with 10 ml of isopropanol and 0.1 ml of BF$_3$.etherate and then subjected to reflux for 30 minutes for ester exchange reaction with isopropanol, whereby isopropyl 5-methylbrendane-4-one-2-carboxylate was obtained. In view of the result of ester exchange reaction, it was confirmed that the reaction product before the ester exchange reaction was methyl 5-methylbrendane-4-one-2-carboxylate.

MSm/e: 208.

IR: 2960, 2875, 1730, 1720, 1465, 1450, 1370, 1200, 1040.

EXAMPLE 3

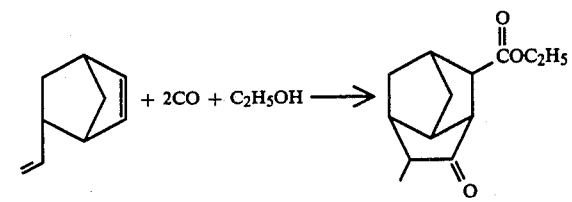

A similar reaction was carried out as in Example 1, except that 240 ml of ethanol was used in place of isopropanol, and then the reaction product was subjected to distillation to obtain 2.8 g of ethyl 5-methylbrendane-4-one-2-carboxylate (112°–114° C./1 mmHg).

MSm/e: 222.

Ultimate Analysis ($C_{13}H_{18}O_3$): Cald. (%): C; 70.3, H; 8.1, O; 21.6. Found (%): C; 70.1, H; 8.0, O; 21.9.

IR: 2960, 2875, 1730, 1720, 1470, 1450, 1370, 1200, 1045.

EXAMPLE 4

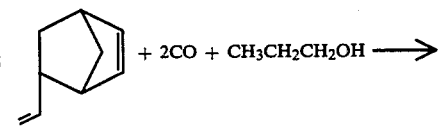

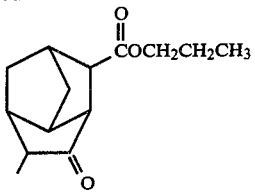

A similar reaction was carried out as in Example 1, except that 240 ml of n-propanol was used in place of isopropanol, and then the reaction product was subjected to distillation to obtain 2.2 g of propyl 5-methylbrendane-4-one-2-carboxylate (123°–125° C./1 mmHg).

MSm/e: 236.

Ultimate Analysis ($C_{14}H_{20}O_3$): Cald. (%): C; 71.2, H; 8.5, O; 20.3. Found (%): C; 71.1, H; 8.7, O; 20.2.

IR: 2960, 2875, 1730, 1720, 1470, 1450, 1370, 1200, 1060, 1050.

EXAMPLE 5

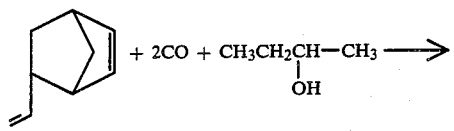

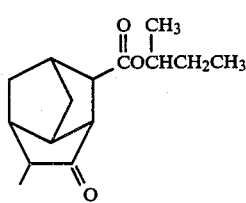

A similar reaction was carried out as in Example 1, except that 240 ml of sec-butanol was used in place of isopropanol, and then the reaction product was subjected to distillation to obtain 7.1 g of sec-butyl 5-methylbrendane-4-one-2-carboxylate (135°–137° C./1 mmHg).

MSm/e: 250.

Ultimate Analysis ($C_{15}H_{22}O_3$): Cald. (%): C; 72.0, H; 8.8, O; 19.2. Found (%): C; 72.1, H; 8.7, O; 19.2.

IR: 2960, 2875, 1730, 1720, 1460, 1450, 1370, 1200, 1120, 1100.

EXAMPLE 6

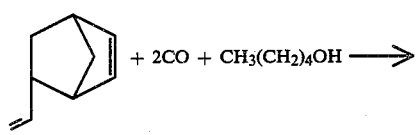

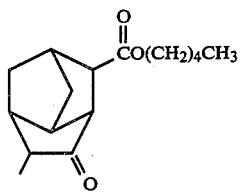

A similar reaction was carried out as in Example 1, except that 240 ml of n-pentanol was used in place of isopropanol, and then the reaction product was subjected to distillation to obtain 2.1 g of n-pentyl 5-methylbrendane-4-one-2-carboxylate (154°–156° C./1 mmHg).

MSm/e: 264.

Ultimate Analysis ($C_{16}H_{24}O_3$): Cald. (%): C; 72.7, H; 9.1, O; 18.2. Found (%): C; 72.6, H; 9.0, O; 18.4.

IR: 2960, 2875, 1730, 1720, 1470, 1450, 1370, 1200, 1050.

EXAMPLE 7

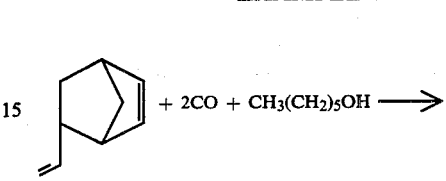

A similar reaction was carried out as in Example 1, except that 240 ml of n-hexanol was used in place of isopropanol, and then the reaction product was subjected to distillation to obtain 1.8 g of n-hexyl 5-methylbrendane-4-one-2-carboxylate (167°–169° C./1 mmHg).

MSm/e: 278.

Ultimate Analysis ($C_{17}H_{26}O_3$): Cald. (%): C; 73.9, H; 8.7, O; 17.4. Found (%): C; 73.9, H; 8.7, O; 17.4.

IR: 2960, 2875, 1730, 1720, 1470, 1450, 1370, 1200, 1055.

EXAMPLE 8

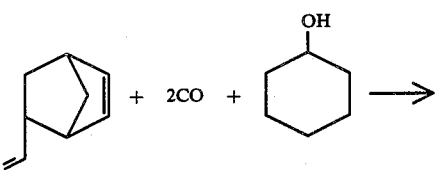

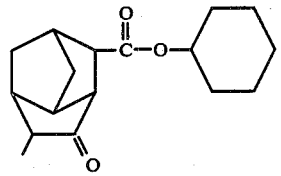

A similar reaction was carried out as in Example 1, except that 240 ml of cyclohexanol was used in place of isopropanol, and then the reaction product was subjected to distillation to obtain 3.5 g of cyclohexyl 5-methylbrendane-4-one-2-carboxylate (160°–162° C./1 mmHg).

MSm/e: 276.

Ultimate Analysis ($C_{17}H_{24}O_3$): Cald. (%): C; 73.9, H; 8.7, O; 17.4. Found (%): C; 73.7, H; 8.8, O; 17.5.

IR: 2960, 2875, 1730, 1720, 1460, 1450, 1200, 1120, 1100, 1070.

EXAMPLE 9

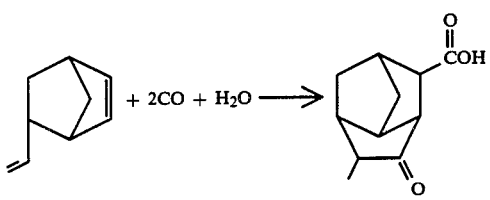

A similar reaction was carried out as in Example 1, 1 except that 120 ml of 1,4-dioxane and 120 ml of water were used in place of isopropanol. After allowing to stand the reaction mixture for cooling, the reaction mixture was discharged from the autoclave and added with 200 ml of diethyl ether, and then rinsed with 200 ml of a 10% aqueous solution of $H_2SO_4$ for two times to remove alcohol and pyridine. Thereafter, using 100 ml of a saturated aqueous solution of sodium hydrogencarbonate for each time, the carboxylic acid was extracted from the organic phase for two times. The aqueous phase was then neutralized with a 10% aqueous solution of $H_2SO_4$ to separate the free carboxylic acid which was extracted with 50 ml of diethyl ether. The organic phase was dried with sodium sulfate anhydride, and then the ether was distilled off to obtain 22 g of white powders.

The powders were added with 100 ml of isopropanol and 0.5 ml of concentrated sulfuric acid, followed by reflux for 3 hours, and then subjected to gas chromatography to find that 3.1 g of isopropyl 5-methylbrendane-4-one-2-carboxylate was produced.

EXAMPLE 10

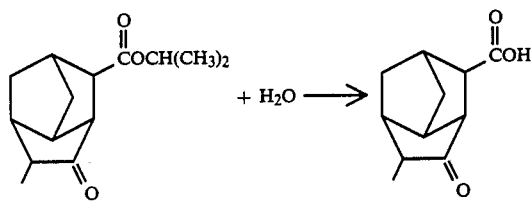

1 g of the isopropyl 5-methylbrendane-4-one-2-carboxylate prepared by Example 1 was mixed with 10 ml of a 10% aqueous solution of NaOH, and the mixture was boiled for 2 hours under vigorous agitation. After the completion of reaction, the reaction mixture was neutralized with a 10% aquesous solution of $H_2SO_4$ until the pH value of the reaction mixture reached pH 4. The separated free carboxylic acid was extracted by 20 ml of diethyl ether, and the organic phase was dried with sodium sulfate anhydride. Then, diethyl ether was distilled off to obtain 0.75 g of 5-methylbrendane-4-one-2-carboxylic acid in the form of white powders.

MSm/e: 194.

Ultimate Analysis ($C_{11}H_{14}O_3$): Cald. (%): C; 68.1, H; 7.2, O; 24.7. Found (%): C; 68.3, H; 7.0, O; 24.7.

EXAMPLE 11

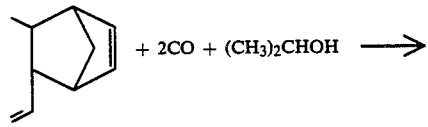

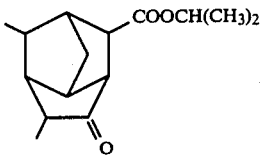

A similar reaction was carried out as in Example 1, except that 80 g (0.6 mol) of 6-methyl-5-vinyl-2-norbornene was used in place of 5-vinyl-2-norbornene and then the reaction product was subjected to distillation to obtain 5.8 g of isoproply 5,9-dimethylbrendane-4-one-2-carboxylate (132°-134° C./1 mmHg).

MSm/e: 250.

Ultimate Analysis ($C_{15}H_{22}O_3$): Cald. (%): C; 72.0, H; 8.8, O; 19.2. Found (%): C; 71.8, H; 8.8, O; 19.4.

IR: 2960, 2875, 1730, 1720, 1460, 1450, 1370, 1200, 1100.

EXAMPLE 12

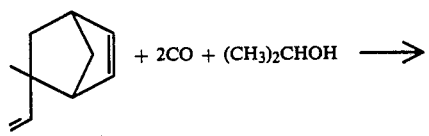

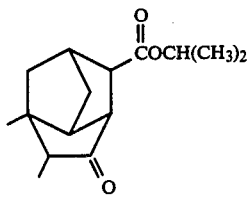

A similar reaction was carried out as in Example 1, except that 80 g (0.6 mol) of 5-methyl-5-vinyl-2-norbornene was used in place of 5-vinyl-2-norbornene and then the reaction product was subjected to distillation to obtain 2.1 g of isopropyl 5,6-dimethylbrendane-4-one-2-carboxylate (130°-132° C./1 mmHg).

MSm/e: 250.

Ultimate Analysis ($C_{15}H_{22}O_3$): Cald. (%): C; 72.0, H; 8.8, O; 19.2. Found (%): C; 72.1, H; 8.8, O; 19.1.

IR: 2960, 2875, 1730, 1720, 1460, 1450, 1370, 1200, 1100.

EXAMPLE 13

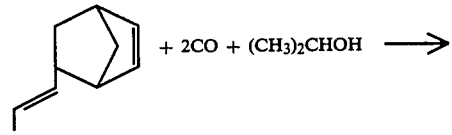

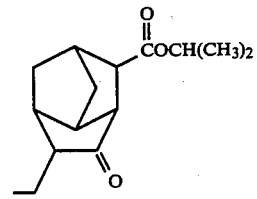

A similar reaction was carried out as in Example 1, except that 80 g of propenylnorbornene was used in place of 5-vinyl-2-norbornene and then the reaction product was subjected to distillation to obtain 0.9 g of isopropyl 5-ethylbrendane-4-one-2-carboxylate (130°–132° C./1 mmHg).

MSm/e: 250.

Ultimate Analysis ($C_{15}H_{22}O_3$): Cald. (%): C; 72.0, H; 8.8, O; 19.2. Found (%): C; 72.0, H; 8.8, O; 19.1.

IR: 2960, 2875, 1730, 1720, 1460, 1450, 1370, 1200, 1100.

EXAMPLE 14

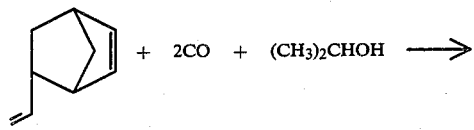 + 2CO + $(CH_3)_2CHOH \longrightarrow$

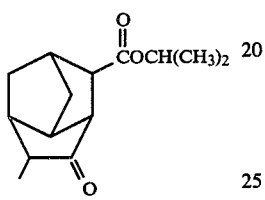

Into a 500 ml stainless steel autoclave, charged were 72 g (0.6 mol) of 5-vinyl-2-norbornene, 240 ml of isopropanol, 0.7 g (1 millimol) of $PdCl_2(PPh_3)_2$ and 0.52 g (2 millimols) of $PPh_3$, and 80 kg/cm² of CO was introduced into the autoclave at the room temperature and then the temperature of the content in the autoclave was raised to 120° C. After reacting for 10 hours, the reaction mixture was cooled and then discharged from the autoclave and subjected to distillation to obtain 2.0 g of isopropyl 5-methylbrendane-4-one-2-carboxylate.

Although the present invention has been described with reference to the specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A derivative of brendane represented by the following formula of:

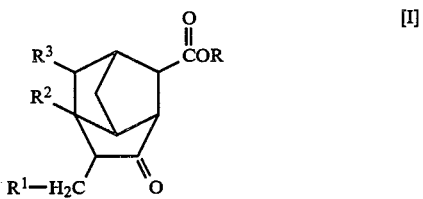

wherein R is a hydrogen atom or a hydrocarbon group selected from the group consisting of methyl, ethyl, n-propyl, isopropyl, sec-butyl, n-pentyl, n-hexyl and cyclohexyl groups, and $R^1$ to $R^3$ each represent a hydrogen atom or a methyl group.

* * * * *